(12) United States Patent
Collins, Sr. et al.

(10) Patent No.: US 10,330,573 B2
(45) Date of Patent: Jun. 25, 2019

(54) RAPID SAMPLE PREPARATION FOR ANALYTICAL ANALYSIS USING DISPERSIVE ENERGIZED EXTRACTION

(71) Applicant: CEM Corporation, Matthews, NC (US)

(72) Inventors: Michael J. Collins, Sr., Matthews, NC (US); Joseph J. Lambert, Charlotte, NC (US); Matthew N. Beard, Huntersville, NC (US); Paul C. Elliott, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 51 days.

(21) Appl. No.: 15/644,920

(22) Filed: Jul. 10, 2017

(65) Prior Publication Data

US 2019/0011337 A1    Jan. 10, 2019

(51) Int. Cl.
*G01N 1/40* (2006.01)
*G01N 1/34* (2006.01)
(Continued)

(52) U.S. Cl.
CPC ....... *G01N 1/4055* (2013.01); *B01D 11/0265* (2013.01); *G01N 1/34* (2013.01);
(Continued)

(58) Field of Classification Search
CPC .................................................. G01N 1/4055
See application file for complete search history.

(56) References Cited

U.S. PATENT DOCUMENTS 2,643,940 A    6/1953  Stevens
4,265,860 A    5/1981  Jennings
(Continued)

FOREIGN PATENT DOCUMENTS

AU    2018204538    8/2018
CN    106018016     10/2016
(Continued)

OTHER PUBLICATIONS

Frenich A.G. et al., "Determination of Pesticides in Food of Animal Origin" in Tadeo J.L. (Ed), "Analysis of Pestcides in Food and Environmental Samples," CRC Press, 2008, pp. 177-207.
(Continued)

*Primary Examiner* — Krishnan S Menon
*Assistant Examiner* — Dwan A Gerido
(74) *Attorney, Agent, or Firm* — Philip Summa

(57) ABSTRACT

An extraction method for preparing samples for analytical analysis is disclosed. The method includes the steps of placing a sample matrix containing one or more analytes in a heat conductive sample cup, positioning the heat conductive sample cup in a pressure-resistant reaction chamber, dispensing solvent into the heat conductive sample cup, dispersing the solvent and the sample matrix in the sample cup in the reaction chamber, heating the sample matrix and the extraction solvent in the heat conductive sample cup in the reaction chamber to a temperature at which the dispensed solvent generates an above-atmospheric pressure, and releasing the extraction solvent extract from the sample cup at atmospheric pressure.

9 Claims, 4 Drawing Sheets

(51) Int. Cl.
  *B01D 11/02* (2006.01)
  *G01N 30/06* (2006.01)
  *G01N 1/44* (2006.01)
  *B01D 11/04* (2006.01)

(52) U.S. Cl.
  CPC ........ *G01N 1/4022* (2013.01); *B01D 11/0257* (2013.01); *B01D 11/0423* (2013.01); *G01N 1/44* (2013.01); *G01N 30/06* (2013.01); *G01N 2001/4061* (2013.01); *G01N 2030/062* (2013.01)

(56) References Cited

U.S. PATENT DOCUMENTS

| | | | |
|---|---|---|---|
| 4,429,049 A | 1/1984 | Rogers | |
| 5,017,500 A | 5/1991 | Langer | |
| 5,268,103 A * | 12/1993 | Jameson | B01D 11/0203 210/634 |
| 5,272,094 A | 12/1993 | Barker | |
| 5,344,571 A | 9/1994 | Mendershausen | |
| 5,447,077 A * | 9/1995 | Lautenschlager | B01D 1/0017 422/430 |
| 5,601,707 A | 2/1997 | Clay | |
| 5,620,659 A | 4/1997 | Revesz | |
| 5,653,885 A | 8/1997 | Jameson | |
| 5,660,727 A | 8/1997 | Gleave | |
| 5,750,008 A | 5/1998 | Lautenschlaeger | |
| 5,785,856 A | 7/1998 | Gleave | |
| 5,858,178 A | 1/1999 | Lautenschlaeger | |
| 5,932,095 A | 8/1999 | Walters | |
| 6,048,457 A | 4/2000 | Kopaciewicz | |
| 6,086,767 A | 7/2000 | Walters | |
| 6,221,655 B1 | 4/2001 | Fung | |
| 6,794,127 B1 | 9/2004 | Lafferty | |
| 6,803,237 B2 | 10/2004 | Manganini | |
| 8,569,072 B2 | 10/2013 | Halverson | |
| 8,901,471 B2 | 12/2014 | Visinoni | |
| 9,574,799 B2 | 2/2017 | Buese | |
| 9,739,692 B2 | 8/2017 | Srinivasan | |
| 2007/0275445 A1 | 11/2007 | De Bont | |
| 2011/0005932 A1 | 1/2011 | Jovanovich | |
| 2011/0233203 A1* | 9/2011 | Visinoni | B01D 11/0211 219/756 |
| 2013/0233093 A1 | 9/2013 | Pohl | |
| 2013/0316466 A1 | 11/2013 | Srinivasan | |
| 2013/0337132 A1 | 12/2013 | Fenna | |
| 2014/0114084 A1 | 4/2014 | Hamler | |
| 2014/0193303 A1 | 7/2014 | Ellis | |
| 2015/0119592 A1 | 4/2015 | Hamler | |
| 2015/0258521 A1* | 9/2015 | McAdams | B01J 19/0053 422/49 |
| 2016/0303490 A1 | 10/2016 | Ellis | |
| 2016/0370035 A1 | 12/2016 | Hofer | |
| 2016/0370357 A1 | 12/2016 | Lucas | |

FOREIGN PATENT DOCUMENTS

| | | |
|---|---|---|
| CN | 107831252 | 3/2018 |
| DE | 2250933 | 5/1974 |
| EP | 0932355 | 8/1999 |
| EP | 2371437 | 10/2011 |
| EP | 3072568 | 9/2016 |
| FR | 2196831 | 3/1974 |
| GB | 380954 | 9/1932 |
| GB | 477567 | 1/1938 |
| GB | 530345 | 12/1940 |
| GB | 613568 | 11/1948 |
| GB | 683121 | 11/1952 |
| GB | 776938 | 6/1957 |
| GB | 845131 | 8/1960 |
| GB | 1012545 | 12/1965 |
| GB | 1065720 | 4/1967 |
| GB | 1074231 | 7/1967 |
| GB | 1123847 | 8/1968 |
| JP | H08029432 | 2/1996 |
| JP | H08338832 | 12/1996 |
| JP | 2005214785 | 8/2005 |
| JP | 2016101166 | 6/2016 |
| WO | 9325842 | 12/1993 |
| WO | 9627417 | 9/1996 |
| WO | 2008101670 | 8/2008 |
| WO | 2015160419 | 10/2015 |
| WO | 2018148225 | 8/2018 |

OTHER PUBLICATIONS

Song, S. et al., "Development, comparison and application of sorbent-assisted accelerated solvent extraction, microwave-assisted extraction and ultrasonic-assisted extraction for the determinatioin of polybrominated diphenyl ethers in sediments," Journal of Chromatography A, 2016, vol. 1475, pp. 1-7.

How to Keep Grounds Out of Percolated Coffee_Percolator Coffee Pot [retrieved from internet on Jan. 11, 2018]<URL: https://web.archive.org/web/20160317210445/http://percolatorcoffeepot.org/how-to-keep-grounds-out-of-percolated-coffee/> published on Mar. 17, 2016 as per Wayback Machine.

Jacketed vessels for all applications with flexibility to meet the most demanding design; AndersonDahlen Inc., Nov. 5, 2017; accessed Aug. 22, 2018 at https://web.archive.org/web/20171105035338/ https://www.andersondahlen.com/components/vessels/jacketed-vessels.

Richter De et al., Anal Chem 1996, 68, 1033.

Definitions of "adsorption," "organic," "solvent," and "sorbent"—Lewis, Hawley's Condensed Chemical Dictionary, 15th Edition, 2007, John Wiley & Sons.

EPA Method 3545 Pressurized Fluid Extraction (PFE), Rev. 1, Jan. 1998; pp. 10.

Definitions of "adsorb," "loose," "opposite," "sorbent," and "solid,"—Urdang, The Random House College Dictionary, Random House Inc. (1972).

EPA Method 3540C—Soxhlet Extraction, Rev. 3, Dec. 1996, pp. 8.
EPA Method 3550C—Ultrasonic Extraction, Revision 3, Feb. 2007; pp. 17.

EPA Method 8270D—Semivolatile Organic Compouns by Gas Chromatography/Mass Spectrometry (GC/MS), Rev. 4, Jan. 1998, pp. 62.

CRM Catalog No. 727 Base/Neutrals & Acids in Soil, ERA Environmental 2014 Proficiency Testing and Reference Materials, Online Product Catalog, Waters Corporation.

Knowles, D; Dorich, B; Carlson, R; Murphy, B; Francis, E; Peterson, J, Richter, B. "Extraction of Phthalates from Solid Liquid Matrices," Dionex Corporation, 2011, pp. 4.

Consumer Products Safety Commission, Test Method: CPSC-CH-C1001-09.3 Standard Operating Procedure for Determination of Phthalates Apr. 1, 2010; http://www.cpsc.gov/about/cpsia/ CPSC-CH-C1001-09.3.

Safety Data Sheet: Phthalates from Polyethlene in a CRM sample; SPEX CertiPrep CRM-PE001; Metuchen, NJ 08840, 2017; pp. 7.

Arsenault, J.C. Beginner's Guide to SPE Solid-Phase Extraction; 2012, Waters Corporation; pp. 28.

Lehotay, et al., Comparison of QuEChERS sample preparation methods for the analysis of pesticide residues in fruits and vegetables; Journ of Chromatography A, 1217 (2010) 2548-2560.

Kabay et al, Solvent-impregnated resins (SIRs)—Methods of preparation and their applications; Reactive & Functional Polymers 70 (2010) 484-496.

QuEChERS Simplified, Waters Corporation, Jul. 2016, pp. 8.

The Basics: QuEChERS Step by Step; 2013, accessed Dec. 8, 2016 at http://blog.teledynetekmar.com/blog/bid/350968/The-Basics-QuEChERS-Step-by-Step.

AOAC Official Method 2007.01 Pesticide Residues in Food by Acetonitrile Extraction and Partitioning with Magnesium Sulfate, 2007 AOAC International, pp. 9.

Burns, Donald—Automated Sample Preparation, Anaytical Chemistry, vol. 53, No. 12, Oct. 1981.

(56) References Cited

OTHER PUBLICATIONS

Automated Protein and Peptide Sample Preparation for Mass Spec Analysis, Agilent Technologies, 2015, pp. 8.

Solid Phase Extraction, SPE Protocol—Sample Preparation; Orochem Technologies, Inc., 2016, pp. 5.

Co-pending U.S. Appl. No. 15/644,950 for "Rapid Energized Dispersive Solid Phase Extraction (SPE) for Analytical Analysis" filed Jul. 10, 2017.

Co-pending U.S. Appl. No. 15/644,938 for "Instrument for Analytical Sample Preparation" filed Jul. 10, 2017.

Standard Operating Procedure for Soxhlet Extraction of Biomass; accessed Sep. 16, 2018 at https://pdfs.semanticscholar.org/presentation/a96a/47d960bfbcde1f908239ccfaa8fc9d006b22.pdf; 12 pages.

Refluxing a Reaction; accessed Sep. 26, 2018 at http://cactus.dixie.edu/smblack/chemlabs/refluxing_a_reaction.pdf, 1 page.

Practical techniques in organic chemistry (Heating under reflux); accessed Sep. 21, 2018 at https://quizlet.com/137786055/161-practical-techniques-in-organic-chemistry-heating-under-reflex-flashcards/; 2 pages.

Reflux and distillation posted Apr. 30, 2015 on Assist (Australian School Science Information Support for Teachers and Technicians); accessed Sep. 20, 2018 at https://assist.asta.edu.au/print/2802; 6 pages.

Ondruschka et al., Microwave-Assisted Extraction—A State-of-the-Art Overview of Varieties; Chimia 60 (2006); 321-325.

NEOS Microwave Soxhlet; Milestone brochure; date unknown; 6 pages.

Yunjie Ding et al., Determination of Pharmaceuticals in Biosolids using Accelerated Solvent Extraction and Liquid Chromatography/Tandem Mass Spectrometry; Journal of Chromatography A (2010); 24 pages.

ASE 200 Accelerated Solvent Extractor Operator's Manual, Doc. No. 031149, Rev. 4, Dec. 1999; 184 pages.

Van Den Berg, C., In-situ product recovery from fermentation broths, 2010, Doctoral dissertation, TU Delft, Delft University of Technology, 117 pages.

"I use a moka pot to make coffee every morning. I get coffee beans from Starbucks and it tastes good but how can I make it taste even better?" Published Jan. 16, 2015 on Quora.com; accessed at: https://www.quora.com/I-use-a-moka-pot-to-make-coffee-every-morning-I-get-coffee-beans-from-Starbucks-and-it-tastes-good-but-how-can-I-make-it-taste-even-betterhttps://www.quora.com/.

Improved Soxhlet Extraction of Medical Marijuana Oil [viewed on internet on Jan. 7, 2019] < URL: https://www.youtube.com/watch?V=XOLJp8G732g>, published on May 15, 2013.

"General extraction time and solvent type for soxhlet extraction—can anyone help?" [accessed Jan. 7, 2019] < URL: https://www.researchgate.net/post/General-extraction_time_and_solvent_type_for_soxhlet_extraction_can_anyone_help>, published 2013.

Dionex ASE Extraction Thimbles, Thermo Scientific, 2014; 4 pages.

\* cited by examiner

RAPID SAMPLE PREPARATION FOR ANALYTICAL ANALYSIS USING DISPERSIVE ENERGIZED EXTRACTION

RELATED APPLICATION

This application is related to application Ser. No. 15/644,938 filed concurrently herewith for Instrument for Analytical Sample Preparation and application Ser. No. 15/644,950 filed concurrently herewith for Rapid Energized Dispersive Solid Phase Extraction (SPE) for Analytical Analysis.

BACKGROUND

The present invention relates to analytical chemistry, and in particular relates to sample preparation for molecular analysis.

In order to carry out molecular analysis (the task of identifying one or more compounds in a sample) of any product, a sample of the product must be in such a form that it can be easily analyzed by chromatography, spectroscopy, mass spectroscopy and/or nuclear magnetic resonance instrumentation Because these analytical instruments require substantially pure isolated analytes, some intermediate steps, generally referred to as "sample preparation", must be carried out to isolate the compounds of interest from the sample matrix in which they might be found and prepare them for analysis by instrumentation.

The task of identifying one or more compounds in a sample-presents an enormously larger set of possibilities and challenges related to sample preparation. The number of "naturally occurring" compounds (those produced by plants or animals) is immeasurably large, and the capabilities of modern organic and inorganic synthesis have generated—figuratively or literally—a similar number of synthetic compounds.

There is tremendous interest in identification or quantitative measurement for compounds of interest as it relates to industrial processes, and for environmental testing for contaminants in waste water, soil, and air.

Even a small group of recognizable representative samples would include pesticides in food, other synthetic chemicals in food (antibiotics, hormones, steroids), synthetic compositions (benzene, toluene, refined hydrocarbons) in soil, and undesired compositions in everyday items (e.g., Bisphenol-A ("BPA") in polycarbonate bottles and other plastic food packaging.

In general extraction has been a main form of sample preparation; i.e., drawing one or more compounds of interest from a sample by mixing the sample with a solvent into which the desired compound(s) will be extracted from the sample so that it can be measured by an analytical technique.

For several generations (and continuing to date), sample preparation in the form of extraction has been carried out by the well-understood Soxhlet method which was invented in the 19th century. In the Soxhlet technique, a single portion of solvent circulates repeatedly through a sample matrix until extraction is complete. To the extent the Soxhlet method has an advantage, it allows an extraction to continue on its own accord for as long as the boiling flask is heated and the condenser is cold.

This method of extraction can take hours to completely extract the compounds of interest. Other concerns of safety from flammable solvents, hazardous waste and breakable glassware are significant drawbacks to this method.

Another commonly known extraction method uses ultra-sonication; i.e., the irradiation of a liquid sample with ultrasonic (>20 kHz) waves resulting in agitation. Although ultra-sonication has an advantage of speeding up the extraction process the disadvantages are that it is a labor intensive, manual process and uses large amounts of solvents.

In more recent years analytical scale microwave-assisted extraction (MAE) has been utilized. MAE uses microwave energy to heat solvents in contact with a sample in order to partition analytes from the sample matrix into the solvent. The main advantage of MAE is the ability to rapidly heat the sample solvent mixture. When using closed pressurized-vessels the extraction can be performed at elevated temperatures that accelerate the extraction of the compounds of interest from the sample matrix. MAE accelerates the extraction process, but has its disadvantages as well. In the microwave heating process typically a polar solvent is needed to provide dipole rotation and ionic conduction through reversals of dipoles and displacement of charged ions present in the solute and the solvent, limiting non-polar solvent use. MAE uses expensive, high-pressure vessels that do not provide a means of filtering the extract, and they must be cooled before pressure can be released.

In the 1990's automated apparatuses for the extraction of analytes were developed. These apparatuses incorporated solvent extraction in pressurized cells under elevated temperatures and pressures and are referred to as "Pressurized Fluid Extraction" ("PFE") or "Accelerated Solvent Extraction" ("ASE"). PFE has shown to be similar to Soxhlet extraction, except that the solvents are at elevated temperatures where they exhibit high extraction properties. This procedure was first developed by Dionex (Richter D E et al., Anal Chem 1996, 68, 1033). One such PFE automated extraction system (Dionex ASE) is commercially available.

PFE was initially used for environmental contaminants (EPA Method 3545, herbicides, pesticides, hydrocarbons) in soil, sediments and animal tissues but has expanded to use in foods, pharmaceutical products and other biological samples.

PFE provides an efficient extraction, but still has not overcome the major bottlenecks associated with the many steps necessary to prepare a sample for analysis. PFE utilizes multiple-component cells and many steps. The cells are tightly packed with the sample and other packing material to eliminate any void areas in the cell, enhance separation, and avoid channeling. Preparing a cell for analysis can typically take 15 minutes. The cells are pre-pressurized at pressures up to 1500 psi and heated up to 200° C. prior to adding the solvent. Extraction is based on chromatographic principles to force the hot solvent through the column. Cycle times can take up to 20 minutes and the requirements of high pressure lead to secondary disadvantages with respect to cost and maintenance.

Newer PSE or ASE techniques attempt to address some of these difficulties, but still require that the cells be tightly packed, adding to the complexity and overall time required for each extraction.

Sample preparation, although having developed over the years, nevertheless remains the major bottleneck in molecular analysis. Accordingly, although the Soxhlet, Ultrasonication, MAE and PFE techniques have their advantages, each remains relatively time-consuming. As a result, when multiple samples are required or desired to provide necessary or desired information, the time required to carry out any given extraction-based molecular preparation step reduces the number of samples that can be prepared in any given amount of time, thus reducing the amount of information available in any given time interval. To the extent that measurements are helpful or necessary in a continuous process, this represents a longer gap between samples or before an anomalous or troublesome result can be identified.

In summary, current sample preparation techniques are slow, complex, inefficient, require a large number of separate steps, use excess solvent, are difficult to automate, and operate under high liquid pressure.

Accordingly, extraction-based sample preparation continues to be recognized as a major bottleneck in analytical techniques.

SUMMARY

In one aspect the invention is an extraction method for preparing analytes for molecular analysis comprising collecting a cooled extraction solvent extract for analysis that has been drained from a sample cup after the extraction solvent and a sample matrix containing an analyte have been placed into the sample cup and agitated, heated, and pressurized and the solvent extract has thereafter been cooled.

In another aspect the invention is an extraction method for preparing analytes for molecular analysis that includes the steps of placing an extraction solvent and a sample matrix containing an analyte into a sample cup, thereafter agitating, heating, and pressurizing the extraction solvent and the sample matrix in the sample cup to extract the analyte from the heated sample matrix and into the heated extraction solvent, thereafter draining the pressurized heated extraction solvent extract at atmospheric pressure from the sample cup at atmospheric pressure and until the drained extraction solvent extract approaches or reaches ambient temperature, and collecting the cooled extraction solvent extract for analysis.

In yet another aspect the invention is an extraction based sample preparation method that includes the step of placing an extraction solvent and a sample matrix that contains an analyte into a sample cup. The method includes the steps of heating the sample cup, the sample matrix, and the extraction solvent in a pressure-resistant reaction chamber until the temperature generates an above-atmospheric pressure that together with the increased temperature drives the analyte substantially from the sample matrix into the extraction solvent, while agitating the sample matrix and the extraction solvent in the sample cup, and releasing the solvent extract from the sample cup into a cooling coil at atmospheric pressure in which the cooling coil has a length sufficient to substantially cool the solvent extract to ambient or near-ambient temperature.

In yet another aspect the invention is an extraction method for preparing samples for analytical analysis that includes the steps of placing a sample matrix containing one or more analytes in a sample cup, positioning the sample cup in a pressure-resistant reaction chamber, dispensing solvent into the sample cup, dispersing the solvent and the sample matrix in the sample cup in the reaction chamber, heating the sample matrix and the extraction solvent in the sample cup in the reaction chamber to a temperature at which the dispensed solvent generates an above-atmospheric pressure, releasing the extraction solvent extract from the sample cup into a cooling coil that has a length sufficient to reduce the temperature of the solvent extract to ambient or near-ambient temperature in the coil, and collecting the filtered solvent extract from the coil.

In yet another aspect the invention is an extraction based sample preparation method that includes the steps of placing an extraction solvent, and a sample matrix that contains an analyte into a heat conductive sample cup surrounded by a pressure-resistant reaction chamber with the heat conductive sample cup having one opened filtered end, adding extraction solvent to both the inside of the sample cup and to the reaction chamber outside of the sample cup, and heating the solvent in the reaction chamber outside of the sample cup to in turn heat the sample cup, the sample matrix and the extraction solvent until the temperature generates an above-atmospheric pressure that together with the increased temperature drives the analyte substantially from the sample matrix into the extraction solvent, releasing the solvent extract from the sample cup into a cooling tube at atmospheric pressure in which the cooling tube has a length sufficient to substantially cool the solvent extract to ambient or near-ambient temperature.

In yet another aspect the invention is a heated pressurized agitated mixture of an extraction solvent and a sample matrix containing an analyte in a sample cup.

The foregoing and other objects and advantages of the invention and the manner in which the same are accomplished will become clearer based on the followed detailed description taken in conjunction with the accompanying drawings.

DETAILED DESCRIPTION

Figure 1:
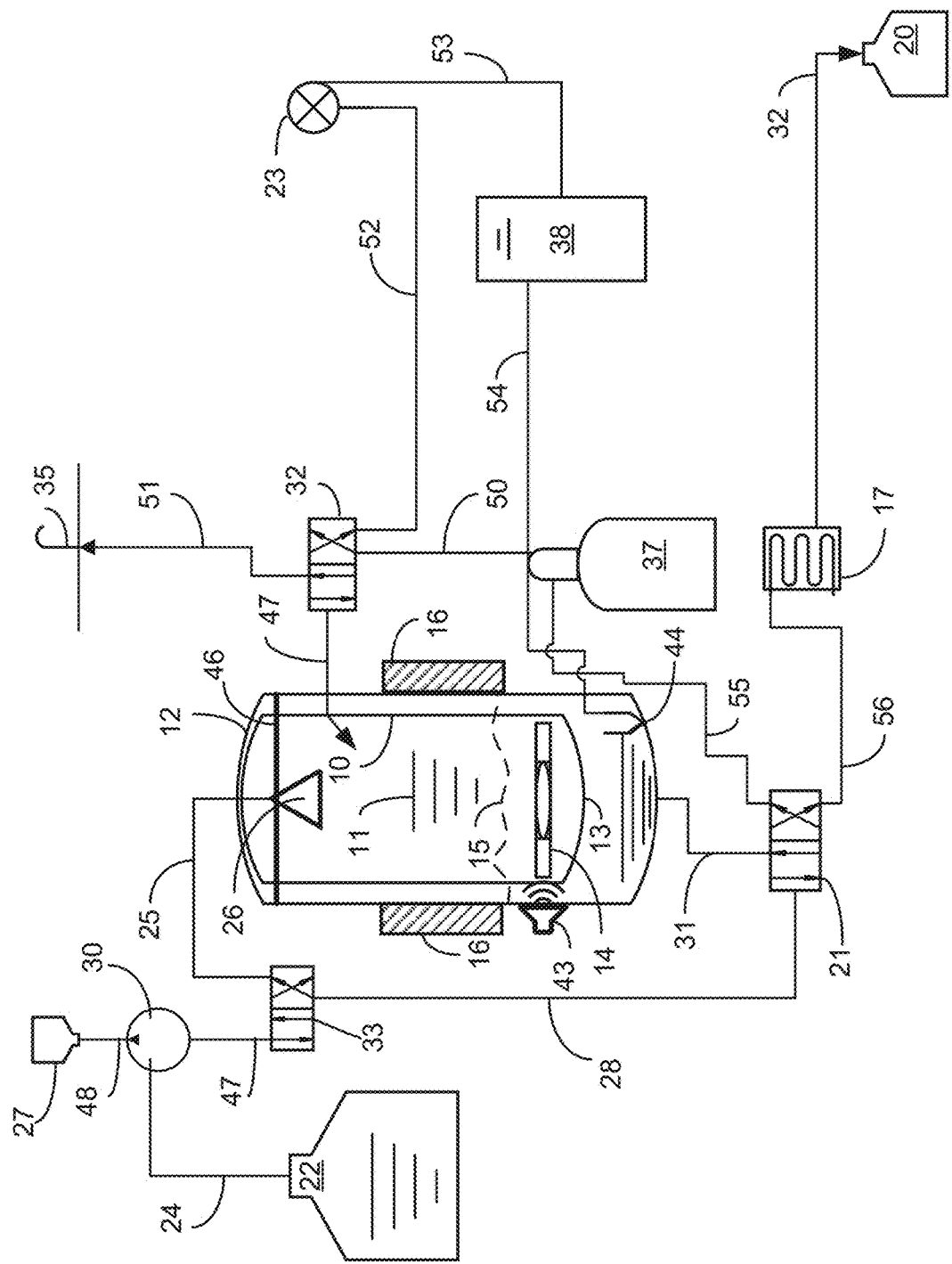
FIG. 1 is a schematic diagram of some of the elements used to carry out the method of the invention.

A number of terms are used herein to describe the method.

The term "solvent" is used in its well understood chemical sense; e.g., "a substance capable of dissolving another substance (solute) to form a uniformly dispersed mixture (solution) at the molecular or ionic size level." The adjective "organic" is used in its well understood sense to "embrace all compounds of carbon" other than certain small molecule combinations of carbon with oxygen, sulfur, and metals, and in some cases halogens. See, Lewis, HAWLEY'S CONDENSED CHEMICAL DICTIONARY, 15th Edition, 2007, John Wiley & Sons The "sample matrix" is the material to be tested for the presence and optionally the amount of analyte.

The "analyte" is the molecular compound of interest. As used herein, "analyte" can include samples with a plurality of analytes within a single sample.

The "solvent extract" is the solution of analyte in a solvent following extraction.

The "sample cup" is the container for the sample matrix and the solvent.

The "collection vessel" is the container that collects the solvent extract following cooling.

In a first aspect the invention is an extraction method for preparing samples for molecular analysis. In the method an extraction solvent and a sample matrix are placed into a sample cup, and the sample cup is positioned in a pressure resistant heating chamber. Typical (but not limiting) sample matrices include food, food packaging, and soil.

As recognized by the skilled person (e.g., US EPA Method 3545) samples should be extracted using a solvent system that gives optimum reproducible recovery of the analytes of interest from the sample matrix, at the concentrations of interest. The choice of extraction solvent depends on the analytes of interest and no single solvent is universally applicable to all analytes.

Typical (but not limiting) solid-liquid extraction solvents for molecular analysis include water, weak acids, weak bases, acetone, hexane 2-propanol, cyclohexane, dichloromethane, acetonitrile, methanol, and mixtures thereof.

As set forth further herein, and without being bound by theory, it appears that the step of heating the reaction chamber to in turn heat the sample cup creates a sufficient pre-equilibrium thermal gradient to assist in mixing and agitating the solvent and the sample. In some embodiments the reaction chamber is pre-pressurized (about 25 psi has been found to be sufficient) to enhance the extraction and potentially enhance the pre-equilibrium thermal gradient and its potential benefits.

In the method of the invention, the sample matrix can also be described as loosely packed in the sample cup. Although the term "loose" is likewise relative, it is used here in its normal sense as being free from anything that binds or restrains and free or released from fastening or attachment (Urdang, THE RANDOM HOUSE COLLEGE DICTIONARY, Random House Inc. (1972)). Because the sample matrix is loose, the addition of solvent from the top, the bottom, or both, helps disperse the sample matrix in the solvent.

The extraction solvent and the sample matrix can also be mixed in the cup in the chamber using an agitating flow of a gas that is otherwise inert to the sample matrix, the analyte or the solvent. Those skilled in the extraction art will recognize that the gas can accordingly be selected based on the known parameters, and that in some cases compressed air will be appropriate while in others nitrogen or hydrogen may be best (with care based upon hydrogen's flammable characteristics). In other cases one of the noble gases (e.g., helium, argon) may be best.

Other mixing techniques can be used (e.g., magnetic stirrers or other mechanical devices), but tend to require more complex instrumentation.

The sample matrix and the solvent are then heated in the sample cup in the reaction chamber to a temperature at which evaporated solvent generates an above-atmospheric pressure. A temperature of 90° C.-180° C. is exemplary (the US Environmental Protection Agency suggests 120° C. for soil), at which temperature typical organic extraction solvents generate a corresponding pressure of 50-250 pounds per square inch (psi). In experiments to date, the time to reach this temperature is about 90 seconds, at which point extraction is substantially complete (it being understood that extraction is an equilibrium process). The pressure generated by the vapor from the solvent is then used to drain the solvent extract from the sample cup into a cooling coil that has a length sufficient to reduce the temperature of the extract to near ambient (e.g., 25° C.) while the solvent extract is in the coil. The solvent extract is then collected from the coil, typically in a collection vessel. In exemplary experiments, metal tubing with a length of about 10 feet tends to provide a dwell time of about 30 seconds, which is sufficient to cool the solvent extract to ambient or near-ambient temperature. Thus, the coil is typically used for space saving purposes, but a coil shape is optional rather than mandatory.

The sample matrix and the extraction solvent can be added in amounts that are typical in this field. For example, a solid matrix is collected in a manner that provides between about 5 or 10 grams (g) of the sample matrix of interest. The amount of extraction solvent will be proportional; typically about 30-100 milliliters (mL).

FIG. 1 is a schematic diagram of the basic elements of an instrument to carry out the method steps of the present invention.

FIG. 1 illustrates a number of the features of the method in the context of a schematic diagram. FIG. 1 illustrates a heat-conductive, pressure-resistant sample cup 10 surrounded by a pressure resistant reaction chamber 12.

In the context of the invention, a typical sample cup is a cylinder form of a heat-conductive material. Because the sample cup 10 is inside the reaction chamber 12, it experiences little or no differential pressure, and thus its mass can be minimized to encourage thermal transfer. In current embodiments, an aluminum cylinder about 3.5 inches (8.9 cm) long and about 1.25 inches (3.2 cm) in diameter, with a wall thickness of about 0.1 inches (2.54 mm) has been found to be appropriate. The terms "heat conductive" or "thermally conductive" are used herein in their well-understood sense to represent materials through which heat passes relatively quickly. The opposite is, of course, the term "insulating," which is likewise well-understood as describing materials through which heat passes more slowly. On that basis, many metals and alloys are particularly useful for the vessel given that such conductivity is one of the distinguishing characteristics of most metals and alloys. Alternatively, many polymeric materials are considered insulating and ordinarily less helpful in the context of the invention. The thermal conductivities of many metals and alloys are published and widely disseminated, and an appropriate metal or alloy can be selected by the skilled person without undue experimentation.

An appropriate sample cup is a cylinder that has an open mouth at one end and a partially open floor at or near the opposite end. Small changes in shape or position (i.e. of the cup, its mouth, or the open end) are, of course, within the expected scope of the invention. The partially open floor can support a filter or filter media and allow solvent extract to drain from the sample cup. The solvent can be dispensed into the sample cup from the top of the sample cup, through the bottom of the sample cup, or both.

The combination of extraction solvent and the sample matrix that contains an analyte (schematically diagrammed by the horizontal lines 11) are maintained in the sample cup 10 using the one open and filtered end 13. The filter medium is designated at 14.

FIG. 1 also shows that additional extraction solvent optionally can be added to the reaction chamber 12 outside of the sample cup 10 as indicated by the dotted line 15 to jacket the sample cup 10. A closure 46 seals the sample cup 10 in the reaction vessel 12.

A heater 16 heats the solvent 15 in the reaction chamber 12 outside of the sample cup 10 to in turn heat the sample cup 10, the sample matrix 11 and the extraction solvent until the temperature generates an above-atmospheric pressure that together with the increased temperature drives the analyte substantially from the sample matrix into the extraction solvent.

The solvent extract is then released by opening the reaction chamber to atmospheric pressure at the open end (e.g., using valve 21) so that the solvent extract can travel to a cooling tube 17 which has a length sufficient to cool the solvent extract to ambient or near-ambient temperatures so that the cooled solvent extract can be collected ready for analysis, for example in a collection vessel 20.

In carrying out preparation of a sample for molecular analysis, the sample matrix is placed in the sample cup 10 which is then placed in the thermally conductive reaction chamber 12. A solvent from a supply 22 is delivered to the sample cup 10 (and thus to the sample matrix) through the valve 33, the associated passageways 24 and 25, and the delivery head 26. A liquid matrix sample can be delivered from a syringe pump 27, 30 and the valve 33. Additionally, solvent can be added to the bottom of the reaction chamber 12 using the valve 33, the line 28, the valve 21, and the line 31.

FIG. 1 also illustrates that the gas agitation is carried out by delivering an inert gas from a supply 37 to a position at or near the bottom of the sample cup using the passageways 40 and 41, as controlled by the valve 42. If a secondary agitation is required, it can be carried out with a device such as the ultrasonic generator 43 which would typically be a piezoelectric transducer.

The draining step takes place when the valve 21 is opened to atmospheric pressure so that the pressurized solvent vapor in the thermally conductive chamber 12 pushes the liquid solvent extract out through the passageway 31, then through the valve 21, and then cooling coil 17. The cooling coil is connected to a collection vessel 20 by the collection tube 32.

Further to FIG. 1 and to complete the description of the possibilities, solvent can flow from the solvent supply 22 to the rotary valve 30 through the line 24. The line 47 connects the rotary valve 30 with the auxiliary valve valve 33. The line 28 connects the auxiliary valve 33 to the gas valve 21 which in turn can use the line 31 to deliver solvent to the bottom of the reaction chamber 12.

The line 48 connects the rotary valve 30 to the syringe 40 so that liquids from the supply 22 can be metered into the syringe 40 from the supply 22 and thereafter from the syringe 40 into the sample cup and through the lines 35 to 25 and the dispenser head 26. The dotted line 15 represents the position of solvent between the sample cup 10 and the reaction chamber 12 when the solvent is used to jacket the sample cup 10.

The gas supply 37 can supply extra pressure to the headspace through the lines 50 and 47 which, along with the gas flow to several other items, is controlled by the valve 32. The line 51 joins the valve 32 to the vent 35.

As part of the gas pressure monitoring, the line 52 connects the valve 32 to the pressure gauge 23 and the pressure gauge 23 is wired to the processor 38 through the communication line 53. The processor 38 is also connected to the thermocouple 44 using the communication line 54 so that monitored combinations of temperature and vapor pressure for various sample extractions can be used to develop helpful standardized information.

In order to provide agitating gas into the bottom of the reaction chamber 12 and the sample cup 10, the gas supply at 37 is also connected to the valve 21 through an appropriate line or tube 184.

A pressure head seal 46 seals the sample cup in the reaction chamber. Line 56 drains solvent from valve 21 to the coil 17, and line 32 drains the coil 17 to the collection vessel 46.

The nature of the method is such that it can be expressed in some additional aspects. In a second aspect, the steps include placing an extraction solvent and the sample matrix containing the analyte into a sample cup. Thereafter, the sample matrix and the extraction solvent are agitated, heated, and pressurized in the sample cup to extract the analyte from the heated sample matrix and into the heated extraction solvent. The pressurized heated extraction solvent extract is then drained at atmospheric pressure from the sample cup and through the cooling coil until the drained extraction solvent extract approaches or reaches ambient temperature. The cooled extraction solvent extract is then collected for analysis.

In FIG. 1 the headspace in the sample cup 10 above the solvent 11 can be pressurized from the gas source 37 using the valve 32 and the line 47.

Obviously, a wide ranging selection is available to the skilled person, and because the invention uses the same solvents and stationary phases as other methods, appropriate choices can be made without undue experimentation.

If a second agitation step is needed, it can be carried out before, or concurrently with, the heating and pressurizing steps, and typically using ultrasonic vibration. Alternatively (or additionally) agitation can be carried out by feeding a gas that is inert to the solvent and the analyte.

As in the previous embodiments, the step of draining the release solvent includes draining the heated release solvent in a coil that has a length sufficient to cool the drained release solvent to approach or reaching ambient temperature while the release solvent is in the coil. At that point, the release solvent containing the analyte is at a temperature ready for molecular analysis in conventional equipment.

Basically, the method of the invention is appropriate for preparing any analyte that is stable at the expected temperatures and pressures.

In each embodiment, solvents can be selected from the group consisting of water, weak acids, weak bases, ethyl acetate, methyl tertiary-butyl ether ("MTBE"), methylene chloride, hexane, acetone, hexane 2-propanol, cyclohexane, acetonitrile, methanol and mixtures thereof, but are not limited to that particular group.

Each embodiment can use an ultrasonic second agitation step during the pressurized heating step.

In each embodiment, the release of the solvent extract to atmospheric pressure is used to drive the solvent extract from the sample cup and into the cooling coil.

In each embodiment, representative heating temperatures are 90-180° C. and representative resulting pressures are between about 50 and 250 psi.

In yet another aspect, the invention can be expressed as the heated pressurized agitated mixture of an extraction solvent and a sample matrix containing an analyte in a sample cup.

EXPERIMENTAL

Example 1

TABLE 1

Environmental Application; Extraction of BNA's from soil

| Method | Sample Size (g) | Solvent (1:1 v/v) | Volume (mL) | Time (minutes) | Temperature (° C.) | Pressure (psi) |
|---|---|---|---|---|---|---|
| Soxhlet | 10 | Hexane/Acetone | 150 | 1440 | 100 | N/A |
| Example 1 | 5 | Hexane/Acetone | 30 | 5 | 100 | <350 |
| ASE | 5 | Dichloromethane/Acetone | 50 | 26 | 100 | 1500 |

Table 1 plots data from the extraction of bases neutrals and acids ("BNA's") from soil comparing Soxhlet (EPA 3540C), the current invention (Example 1), and accelerated solvent extraction (ASE; EPA 3545). The volume and time for the indicated ASE's are taken from a run using the parameters set forth in Dionex application note 317. Analysis was carried out using gas chromatography followed by mass spectroscopy (GCMS; EPA 8270).

The method of the invention uses significantly less solvent and takes significantly less time than the other methods. In particular, the preparation of the ASE extraction cell is generally tedious with over 10 components and steps, whereas the present invention uses just three straightforward pieces. On average, preparation of an ASE extraction cell takes about 15 minutes, while the invention is ready in a few seconds.

TABLE 2

Environmental Application: Extraction of BNA's from soil; CRM Recovery Data (%)

| Analyte | Proficiency |
|---|---|
| Phenol | 60.0 |
| Hexachloroethane | 51.1 |

| Analyte | Soxhlet | % Proficiency Soxhlet |
|---|---|---|
| Phenol | 48.9 | 81.5 |
| Hexachloroethane | 38.6 | 75.5 |

| Analyte | ASE | % Proficiency ASE |
|---|---|---|
| Phenol | N/A | N/A |
| Hexachloroethane | 32.2 | 63 |

TABLE 2-continued

Environmental Application: Extraction of BNA's from soil; CRM Recovery Data (%)

| Analyte | Invention | % Proficiency Invention |
|---|---|---|
| Phenol | 60.2 | 100 |
| Hexachloroethane | 45.6 | 89.2 |

Table 2 summarizes the data by percentage for BNA's in certified reference material (CRM) soil obtained from Waters Corporation (Milford, Mass. 01757 U.S.A.; ERA catalog number 727). As understood by those in the art, the goal is to obtain 100% recovery of the materials known to be present in the CRM sample. For each method, all of the recoveries were within the quality control performance acceptance limits, but the invention (Example 1) recovered all 39 analytes, while ASE recovered only 38, and failed to identify 2-methylnaphthalene. The invention accordingly had the best overall performance in terms of the analytes recovered and the percent recovery of the analytes.

Figure 2:
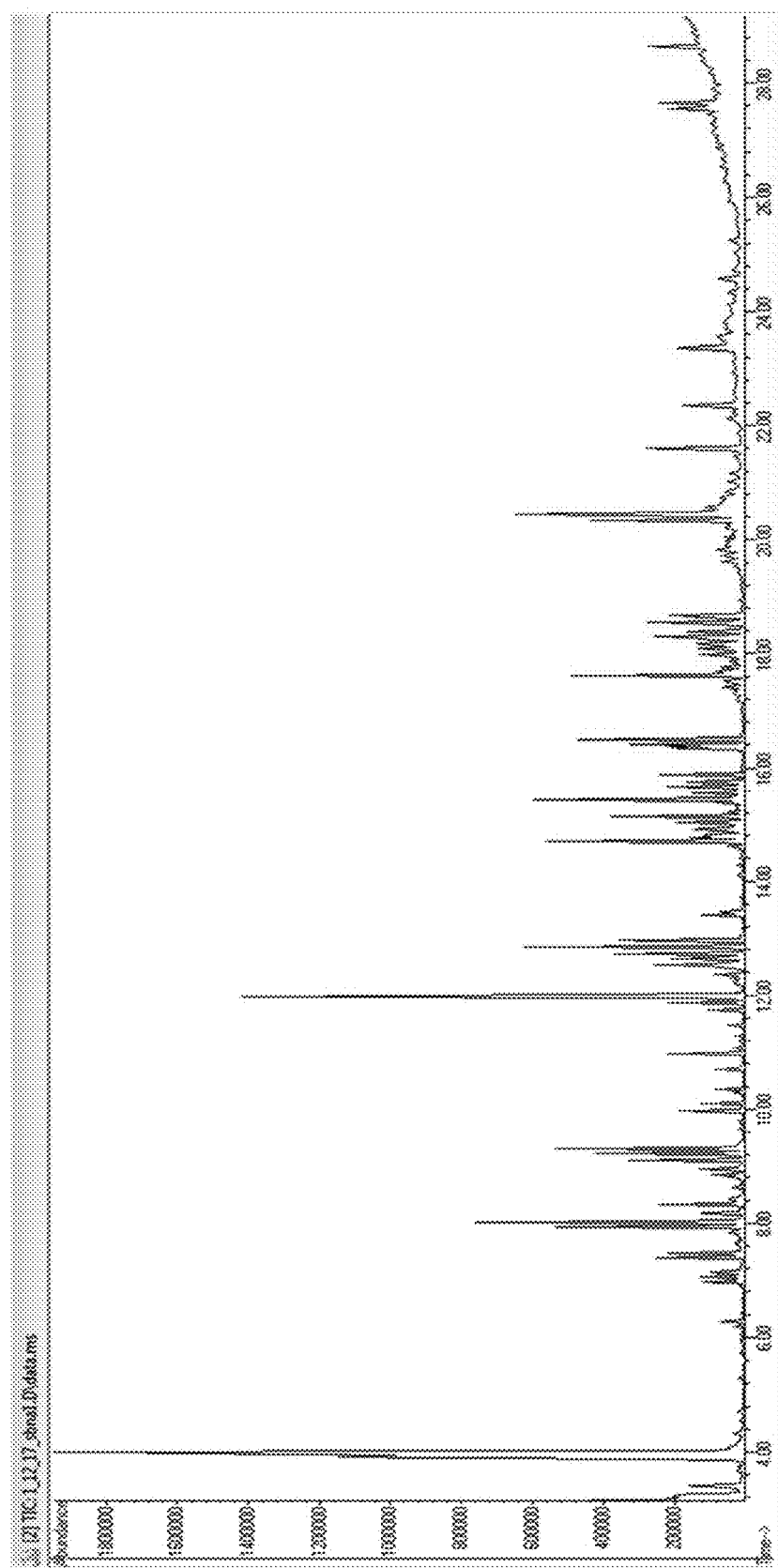
FIG. 2 is an exemplary full scan chromatogram of the BNA CMR extraction based on Example 1.

FIG. 2 is an exemplary full scan chromatogram of the BNA CM R extraction based on Example 1.

Figure 3:
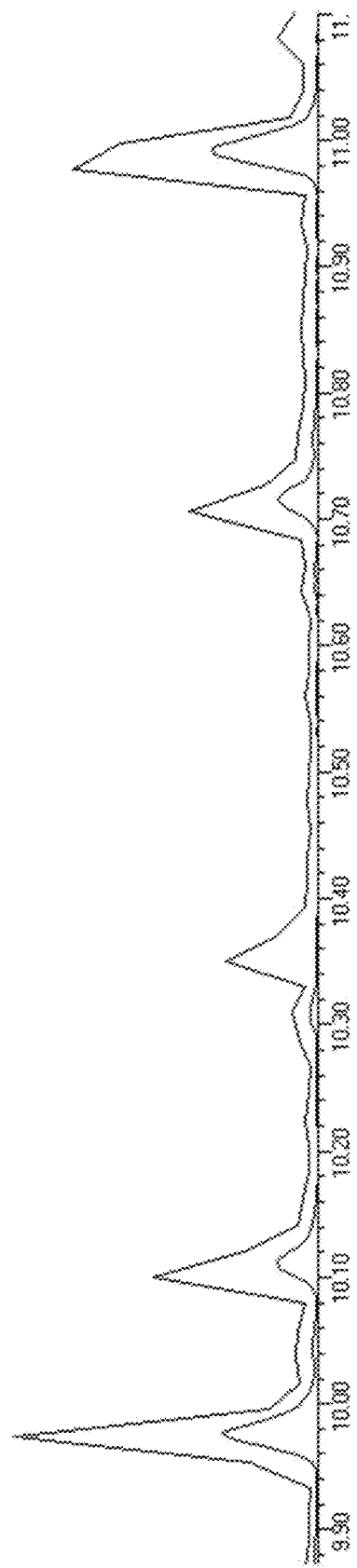
FIG. 3 is an overlay of the Example 1 extraction according to the invention as compared to an ASE extraction

FIG. 3 is an overlay of the Example 1 extraction according to the invention as compared to the ASE extraction. Each of the higher peaks represents the Example 1 extraction which significantly outperformed ASE in recovery. Additionally, the absence of an ASE peak at retention time 10.36 (2-methylnaphthalene) demonstrated the failure of ASE to identify this analyte.

Example 2

TABLE 3

Extraction of Phthalates from Polyethylene

| Method | Sample Size (g) | Solvent (70:30 v/v) | Volume (mL) | Time (minutes) | Temperature ° C. | Pressure psi |
|---|---|---|---|---|---|---|
| Soxhlet | 0.5 | Acetone/Cyclohexane | 150 | 1440 | 100 | N/A |
| Example 2 | 0.5 | Acetone/Cylcohexane | 30 | 10 | 140 | <350 |
| ASE | 0.5 | Hexane | 50 | 63 | 120 | 1500 |

Table 3 is a comparison chart as between Soxhlet, the invention (Example 2), and ASE for the extraction of phthalates from polyethylene. The volume and time for ASE are from a run using the parameters stated in a Dionex publication (Knowles, D; Dorich, B; Carlson, R; Murphy, B; Francis, E; Peterson, J, Richter, B. "Extraction of Phthalates from Solid Liquid Matrices," Dionex Corporation, 2011) and all methods were based off of CPSC-CH-C1001-09.1 (Consumer Products Safety Commission. Test Method: CPSC-CH-C1001-09.3 Standard Operating Procedure for Determination of Phthalates; http://www.cpsc.gov/about/cpsia/CPSC-CH-C1001-09.3.pdf).

Again, the method of the invention (Example 2) used significantly less solvent and took significantly less time than the other methods.

Example 2

TABLE 4

| CRM Recovery Data (%) | | | | | | |
|---|---|---|---|---|---|---|
| Analyte | Soxhlet | Example 2 | % Soxhlet Example 2 | Example 2 w/ Agitation | % Soxhlet Example 2 w/ Agitation | ASE | % Soxhlet ASE |
| Bis (2-ethylhexyl)phthalate | 72.6 | 57.7 | 79 | 73.4 | 101 | 24.3 | 33 |
| Di-n-octyl phthalate | 85.5 | 68.2 | 80 | 80.7 | 94 | 31.4 | 37 |

Table 4 compares the recovery data by percentage for extraction of phthalates from polyethylene in a CRM sample (SPEX CertiPrep CRM-PE001; Metuchen, N.J. 08840, USA). In this experiment agitation was carried out with 30 seconds of both bubbling and sonication prior to heating. Again, the invention (Example 2) recovery data was significantly better than ASE and showed an improvement with the use of agitation. Example 2's results with agitation match Soxhlet data which is considered the "gold standard" for extraction. All analytes in the CRM were recovered for all methods.

Figure 4:
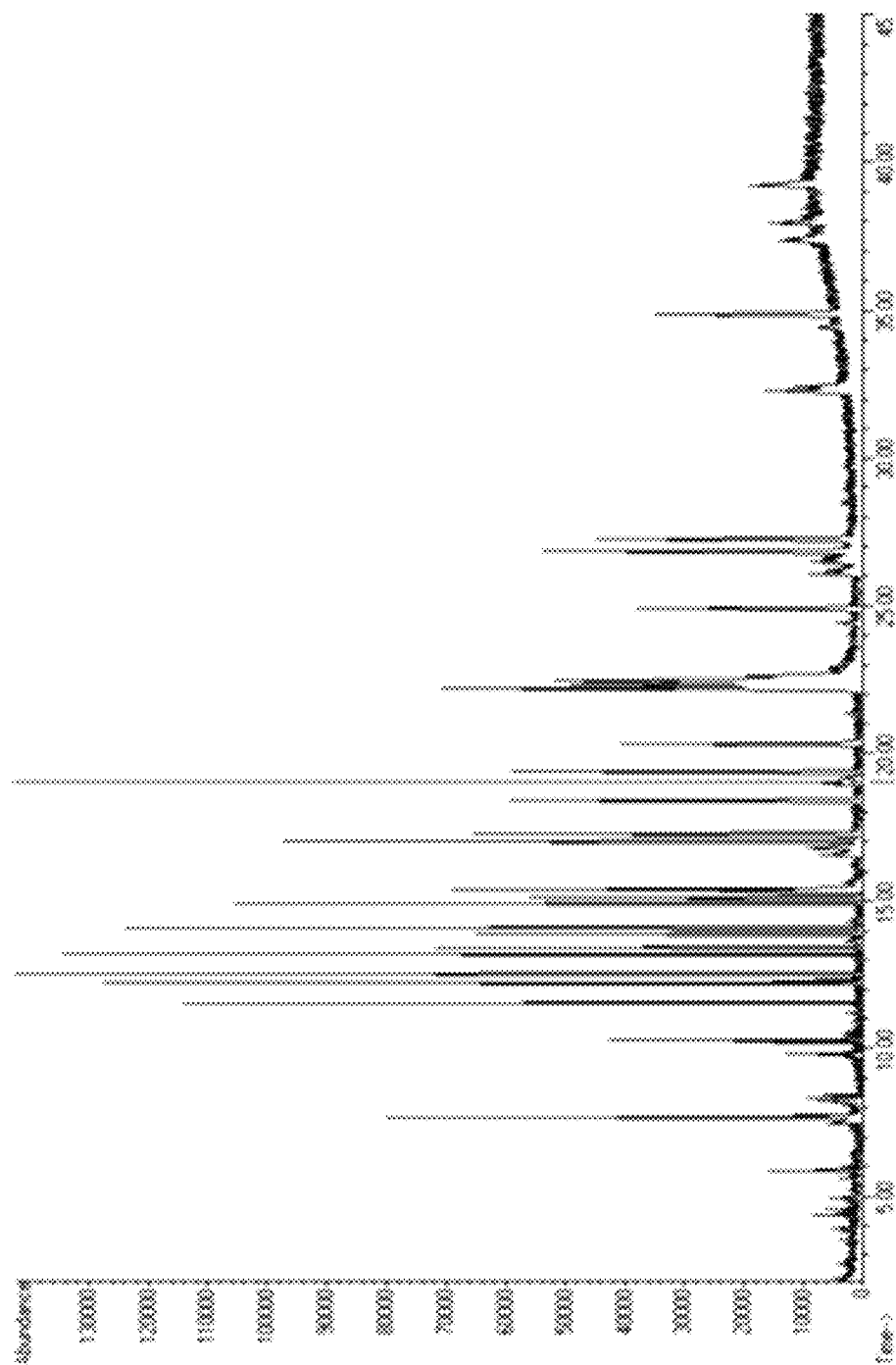
FIG. 4 is a sample full scan chromatogram of the Example 2 polyethylene CRM extraction using the invention.

FIG. 4 is a sample full scan chromatogram of the Example 2 polyethylene CRM extraction using the invention.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. An extraction based sample preparation method comprising:
    placing an extraction solvent, and a sample matrix that contains an analyte into a heat conductive sample cup surrounded by a pressure-resistant reaction chamber with the heat conductive sample cup having one opened filtered end and a mouth opposite from its open filtered end;
    adding liquid extraction solvent to both the inside of the sample cup and to the reaction chamber outside of the sample cup;
    sealing the sample cup between a sealing cover at the cup mouth and an outlet valve at the opposite opened filtered end of the reaction chamber so that a heating step increases the vapor pressure of the liquid extraction solvent above the solvent's vapor pressure at ambient temperature and pressure; and
    heating the liquid extraction solvent in the reaction chamber outside of the sample cup to in turn heat the sample cup, the sample matrix and the liquid extraction solvent until the temperature generates an above-atmospheric pressure that together with the increased temperature drives the analyte substantially from the sample matrix into the liquid extraction solvent;
    releasing the liquid solvent extract from the sample cup into a cooling tube at atmospheric pressure in which the cooling tube has a length sufficient to substantially cool the solvent extract to ambient or near-ambient temperature as the liquid solvent extract travels from the sample cup through the cooling tube and into a collection vessel.

2. An extraction method according to claim 1 wherein the step of placing liquid extraction solvent into the sample cup is carried out from positions selected from the group consisting of the top of the sample cup, the bottom of the sample cup, and both the top and bottom of the sample cup.

3. An extraction method according to claim 1, wherein the open filtered end supports a filter or filter media and allows liquid solvent extract to drain from the sample cup.

4. An extraction method according to claim 1 further comprising dispersing the liquid solvent and the sample matrix by bubbling gas that is inert to the sample matrix through the bottom of the sample cup.

5. A method according to claim 4 wherein the dispersing step is carried out prior to the heating and pressurization of the pressure chamber.

6. An extraction method according to claim 1 further comprising applying ultrasonic agitation during the pressurized heating step.

7. A method according to claim 1 further comprising conductively heating the sample chamber to a temperature of between about 90° C. and 180° C. and generating resulting pressures of between about 50 and 250 psi (about 345 kPa to about 1724 kPa).

8. An extraction method according to claim 1 wherein the liquid extraction solvent is selected from the group consisting of water, weak acids, weak bases, ethyl acetate, methyl tertiary-butyl ether ("MTBE"), methylene chloride, hexane, acetone, hexane 2-propanol, cyclohexane, acetonitrile, methanol and mixtures thereof.

9. An extraction based sample preparation method comprising:
    placing an extraction solvent, and a sample matrix that contains an analyte into a heat conductive sample cup surrounded by a pressure-resistant reaction chamber with the heat conductive sample cup having one opened filtered end and a mouth opposite from its open filtered end;

adding liquid extraction solvent to both the inside of the sample cup and to the reaction chamber outside of the sample cup;

sealing the sample cup between a sealing cover at the cup mouth and an outlet valve at the opposite opened filtered end of the reaction chamber so that the heating step increases the vapor pressure of the liquid extraction solvent above the solvent's vapor pressure at ambient temperature and pressure; and heating the liquid extraction solvent in the reaction chamber outside of the sample cup while ultrasonically agitating the sample matrix and the extraction solvent in the sample cup to in turn heat the sample cup, heat and mix the sample matrix and the liquid extraction solvent until the temperature generates an above-atmospheric pressure that together with the increased temperature drives the analyte substantially from the sample matrix into the liquid extraction solvent;

releasing the liquid solvent extract from the sample cup into a cooling tube at atmospheric pressure in which the cooling tube has a length sufficient to substantially cool the solvent extract to ambient or near-ambient temperature.

\* \* \* \* \*